United States Patent [19]

Ducloux

[11] 4,293,219

[45] Oct. 6, 1981

[54] METHOD AND APPARATUS FOR INSPECTING TRANSPARENT OBJECTS

[75] Inventor: Marcel Ducloux, Le Pecq, France

[73] Assignee: Societe Generale Pour L'Emballage, Paris, France

[21] Appl. No.: 934,827

[22] Filed: Aug. 18, 1978

[30] Foreign Application Priority Data

Aug. 24, 1977 [FR] France .................... 77 25859

[51] Int. Cl.³ .............................................. G01N 21/90
[52] U.S. Cl. .................................. 356/240; 250/223 B; 250/224
[58] Field of Search .............. 356/237, 426, 428, 239; 250/223 B, 224

[56] References Cited

U.S. PATENT DOCUMENTS

| | | | |
|---|---|---|---|
| 3,226,569 | 12/1965 | James | 307/203 |
| 3,349,906 | 10/1967 | Calhoun et al. | 250/227 |
| 3,386,579 | 6/1968 | Schulze et al. | 250/223 B |
| 3,439,178 | 4/1969 | Rottmann | 250/223 B |
| 3,631,255 | 12/1971 | Gender et al. | 250/237 X |
| 3,848,742 | 11/1974 | Krenmayr | 250/223 B X |
| 3,980,890 | 9/1976 | Heckrodt et al. | 250/560 |
| 4,026,414 | 5/1977 | Ellinger | 250/223 B |

FOREIGN PATENT DOCUMENTS

| | | |
|---|---|---|
| 723388 | 12/1965 | Canada . |
| 1286783 | 1/1969 | Fed. Rep. of Germany . |
| 1519309 | 3/1968 | France . |
| 2174551 | 10/1973 | France . |
| 2298101 | 8/1976 | France . |
| 1147836 | 4/1967 | United Kingdom . |

*Primary Examiner*—John K. Corbin
*Assistant Examiner*—Bruce Y. Arnold
*Attorney, Agent, or Firm*—Pennie & Edmonds

[57] ABSTRACT

Transparent objects having at least a localized region with symmetry of revolution are optically inspected by moving them to an examining station, locally illuminating each of them at the examining station with a plurality of circularly scanned fixed light beams, and detecting light from each by a plurality of successively interrogated fixed detection areas. In a preferred embodiment, the illumination is carried out by circular scanning in successive steps about the object with a plurality of differently-oriented, fixed light beams. At least one detection area is interrogated for each illumination step.

33 Claims, 11 Drawing Figures

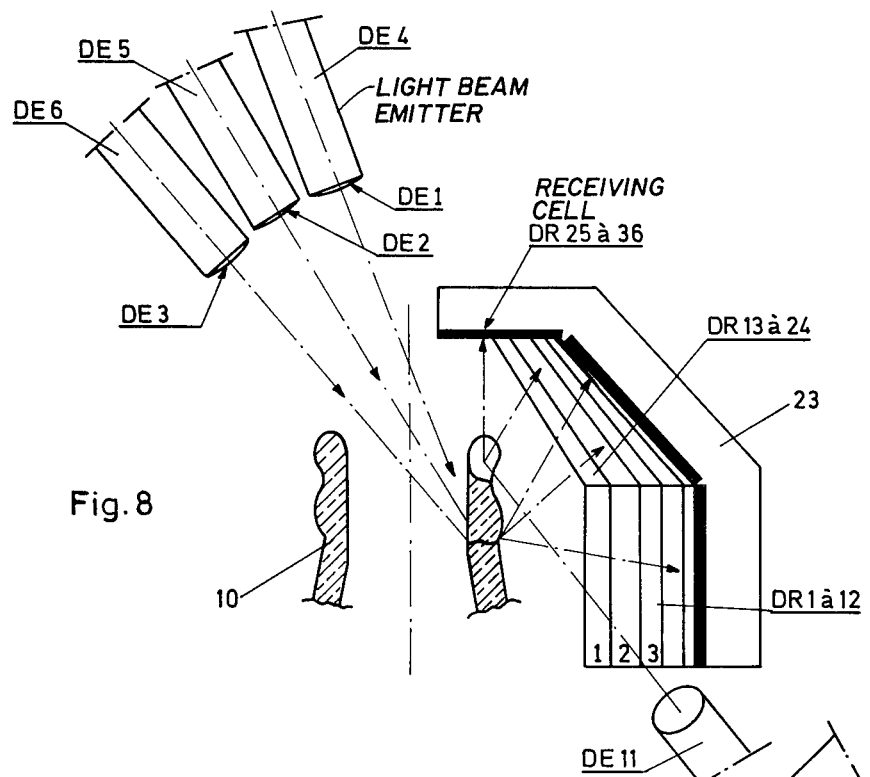
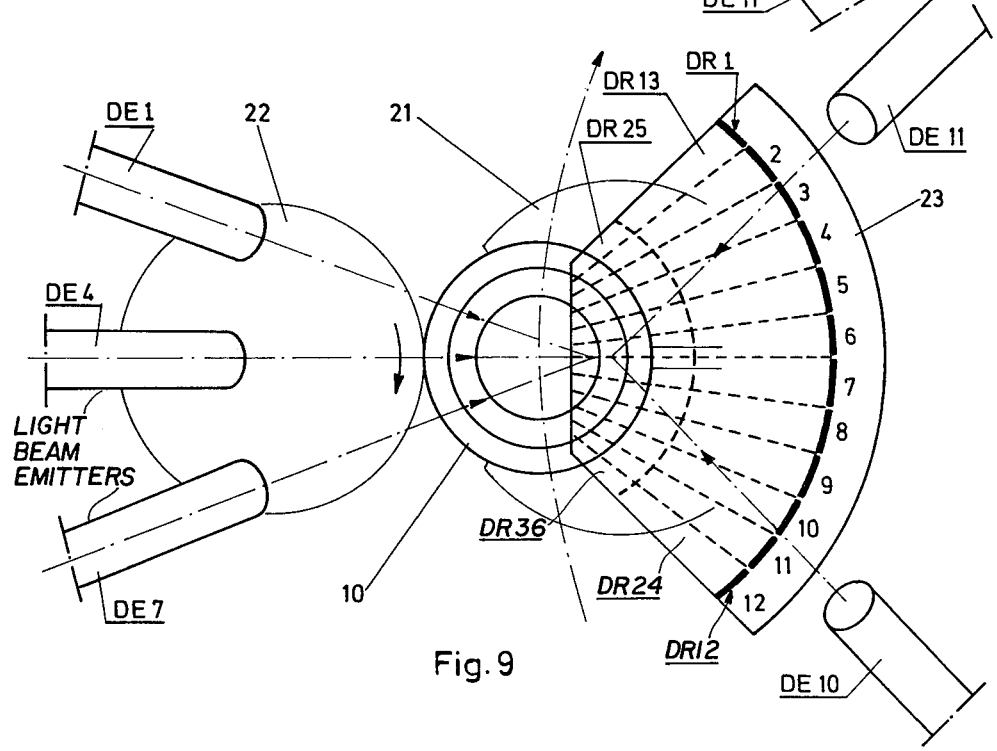

METHOD AND APPARATUS FOR INSPECTING TRANSPARENT OBJECTS

BACKGROUND OF THE INVENTION

1. Field of the Invention

This invention relates to methods and apparatus for the continuous inspection and control of objects which are made of transparent substance, such as glass, in order to eliminate those objects which are defective. More particularly it relates to the inspection of objects such as the mouths of bottles and flasks, which have at least a localized region with symmetry of revolution.

2. Nature and History of the Art

Because of their configuration and the function which they perform, the mouths of glassware vessels often represent a critical region on which the quality of the glassware depends.

One defect that is commonly encountered at the abovementioned region is an internal flaw, referred to as a "glaze", which is likely to cause the glass to break or, at times, to produce an unsatisfactory seal. This defect gives rise to a reflecting surface which most often lies within a radially-oriented vertical plane or within a nearly horizontal plane. It is primarily located at points of variation of cross-section. Another defect which is also encountered is chipping, which affects the evenness of the drinking rim and is responsible for corking or stoppering defects.

The prior art provides for a photo-optic examination of hollow glassware for the purpose of detecting possible glazes. This examination is typically carried out by means of circular scanning which makes use of light beams that illuminate, locally, the neck, rim or other portions of the glassware. The light reflected by a glaze is detected by receivers which control an ejecting device designed to remove the defective items automatically from the conveyor belt.

In order to increase the sensitivity without increasing background noise or other parasitic signals, use is preferably made of a different combination of optical members arranged in a manner appropriate for detecting each given type of defect, i.e. an emitting unit which generates one or more narrow light beams is associated with one or more detecting cells.

It is of value to combine several monitoring devices in the same station wherever possible, but such combination of prior art devices requires careful separation of the different signals, either geometrically or electronically, based on different modulations.

Finally, the apparatus provided by the prior art affords the possibility of presetting, but the adaptation of this apparatus to each particular defect continues to pose a difficult problem. Thus, while such apparatus has been generally satisfactory, it has, nevertheless, been plagued by certain drawbacks and limitations.

One prior art approach involves momentary stopping or slowing down each glassware item and rotating it in order to carry out a complete examination. Apparatus using this approach typically includes a transfer device designed to bring the item from a rectilinear horizontal conveyor belt to a control station. This transfer device is typically highly complex, and its mechanism does not permit the conveying of more than 400 to 500 glassware items per minute. This method is particularly difficult to apply to those glassware items which are noncylindrical in shape, and it undesirably entails an additional handling of the fragile glass object. While this approach can be used at production-line outlets, it is not generally suitable for high speed production lines such as bottling operations.

A second approach involves examining each object with a rotating inspection head as the moving object passes under the control station, without shutting down the conveyor belt or handling or rotating the object. This approach calls for a very high speed rotation head, the speed of which may range within 15,000 to 20,000 revolutions per minute. The head is generally equipped with several associated transmitter-receiver pairs which are precisely oriented with respect to one another so as to delimit different inspection areas or to detect different defects. Nonetheless, the number of examinations made per unit of time remains relatively limited because the apparatus will not operate on objects that are moved too rapidly by the conveyor belt.

OBJECTS OF THE INVENTION

This invention has as its object a method for continuously inspecting and controlling hollow-glassware objects which move by at high rates of speed of up to 2,000 units per minute or more which method is free from the above-mentioned drawbacks.

This invention also has as its object apparatus which embodies the method, which has a high detection sensitivity and which operates consistently over a long period of time.

The invention also seeks to provide a number of modifications which are adapted to detect and control, at the required speed, all of the types of defects which are commonly encountered, i.e.: vertical glazes, horizontal glazes, and chipping.

SUMMARY OF THE INVENTION

In accordance with the invention, a transparent object is inspected by locally illuminating it with a plurality of circularly scanned, fixed light beams. Light from the illuminated object is picked up by a plurality of successively interrogated fixed detection areas disposed along a detection surface. The detection areas yield signals which, when sorted and amplified, are indicative of the light response of the object. In a preferred embodiment, the illumination is carried out by circular scanning in successive steps about the object with a plurality of differently-oriented, fixed light beams. At least one detection area is interrogated for each illumination step.

BRIEF DESCRIPTION OF THE DRAWINGS

The nature, advantages, and various additional features of the invention will appear more fully upon consideration of the various illustrated embodiments to be described in detail in connection with the accompanying drawings.

In the drawings:

FIG. 8 is an elevation view of yet a further modification of the invention which employs mechanical scanning and which combines several different controls;

FIG. 9 is a plan view of the apparatus of FIG. 8;

DETAILED DESCRIPTION

1. General Principle With Electronic Scanning

Figure 1:
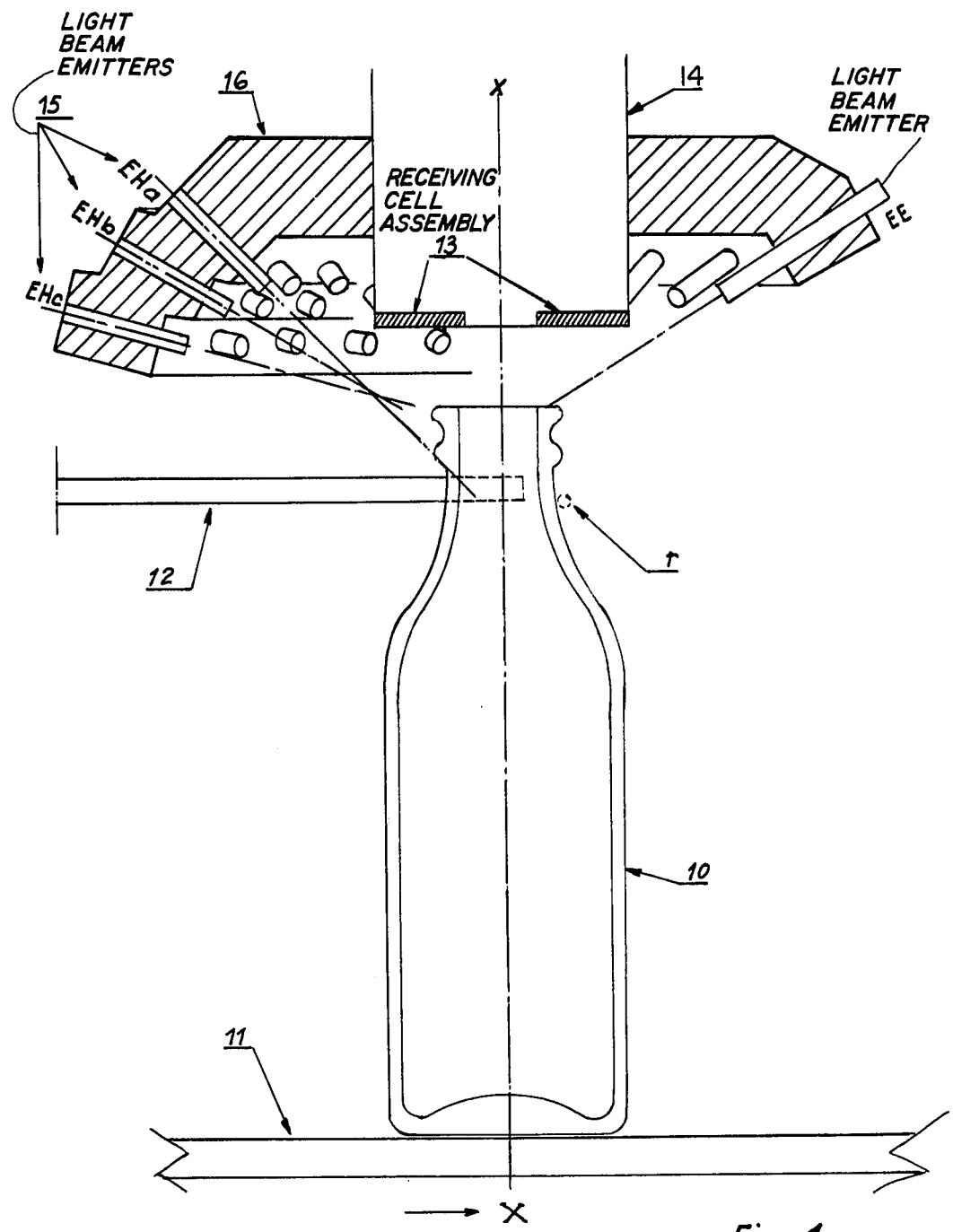
FIG. 1 is a longitudinal cross-section in elevation along the plane of glassware travel of an electronic scanning device in accordance with the invention.

Referring to the drawings, FIG. 1 shows a bottle 10 having a vertical axis of symmetry—XX, placed on a horizontal conveyor belt 11. The conveyor belt is provided with a guiding member such as a rail 12 and a presence-detecting system which includes a light source (not shown) and a photoelectric cell (not shown), the system being physically depicted by light ray r which is propagated perpendicularly to the plane of the figure. The device consists of an assembly 13 of light detecting receiving cells, such as photoelectric cells which are circumferentially arranged at the bottom of tube 14 and a coaxial ring of light beam emitters 15, mounted around tube 14 on a bracket 16. Both the receiving cells and the emitters are connected to an electronic circuit described hereinbelow.

FIG. 1 shows two exemplary embodiments of emitter rings 15, whose bracket 16 is provided with housings in which the emitters are arranged, and the relative positioning of the emitters with respect to the rim of bottle 10 and to the cells of receiver assembly 13. The right-hand portion illustrates an embodiment for detecting defects, such as chipping, which affect the drinking-brim plane surface. The ring is a single one with the emitters EE arranged such that all of the light beams, acting in turn, completely illuminate the drinking brim surface.

The left-hand portion illustrates an embodiment for detecting horizontal glazes. It comprises a triple emitter ring, with emitters EHa, EHb, and EHc arranged for illuminating the rim over its entire height. In both cases, the receiving cells and the emitters are circumferentially arranged. The tilt of the emitters with respect to the horizontal ranges from 30 to 60 degrees, and they are focused on different points of the rim of bottle 10.

2. Chipping Detection

In this illustrative embodiment, the receiving cells and the emitters each number 36. The scanning is electronic.

Figure 2:
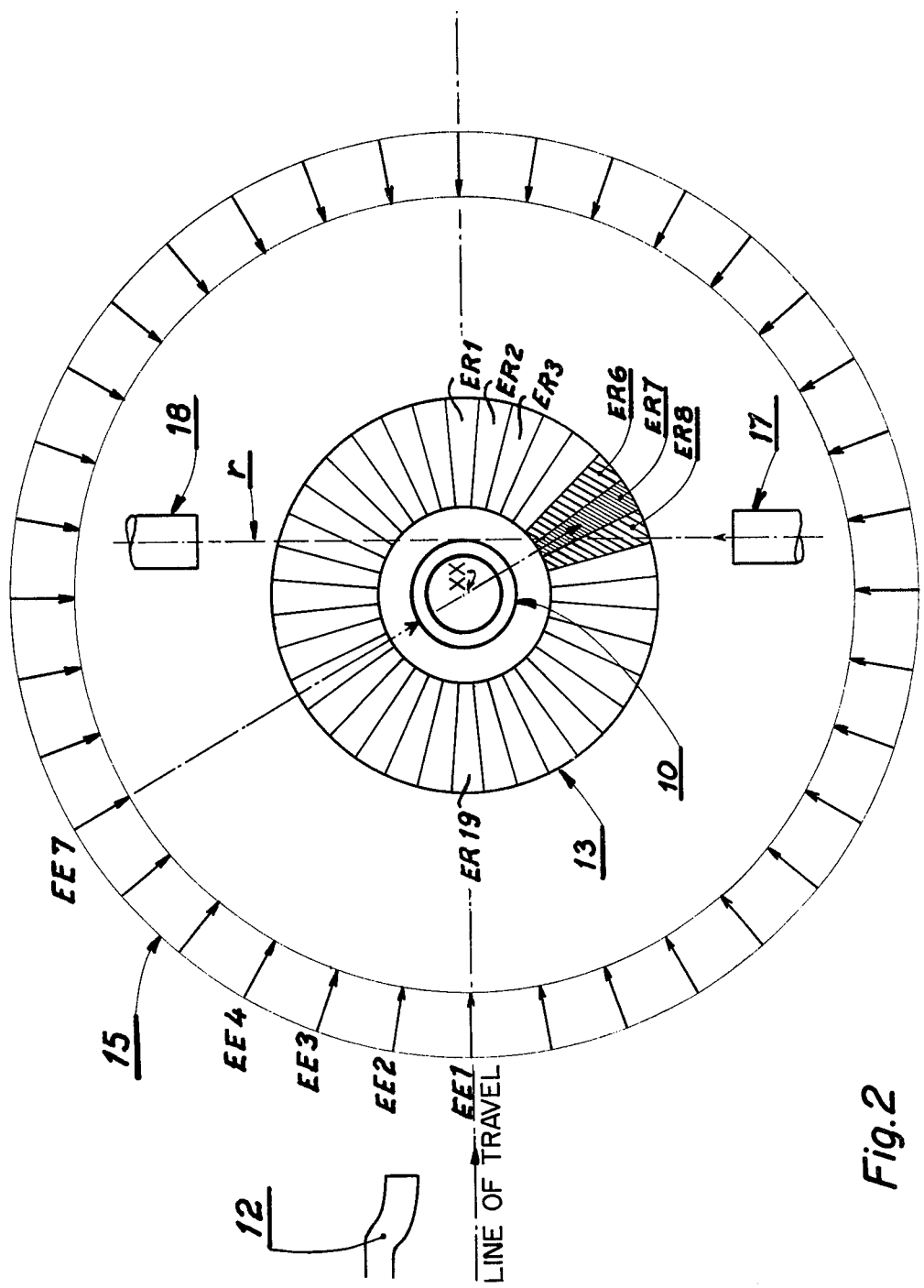
FIG. 2 is a schematic view of the apparatus, in a version which is adapted to detect chipping, along a plane parallel to the conveyor belt.

FIG. 2 depicts schematically, by projection along a plane parallel to the conveyor belt, an inner ring of receiving cells ER1 to ER36 and an outer ring of emitters EE1 to EE36 around the vertical axis of the device. Cells ER1 and ER19 lie along the axis of travel of the glassware items, as do emitters EE1 and EE19.

The bottle 10, which is disposed on the horizontal rectilinear conveyor belt 11, is positioned by guide rail 12. This rail, which is micrometrically adjustable, comes in contact with the neck of the bottle and accompanies it to within a few centimeters of the vertical axis of the device. The axis of symmetry XX of the neck of the bottle is then in a plane which passes through the vertical axis of the device and through the longitudinal axis of the conveyor belt. The thus-positioned bottle cuts off, as it moves, light ray r which is emitted by lamp 17 of the presence detector, whose receiver 18 instantaneously trips the electronically controlled inspection and detection process.

In operation, an emitter situated within a given radial plane is excited and the receiving cell mounted within that plane and opposite the energized emitter is interrogated. All other cells are interdicted. The presence of a chip deflects the light beam and causes the interrogated cell not to respond. Successive pairs of emitters and receivers are excited and interrogated to incrementally inspect the entire circumference of the bottle.

Figure 3:
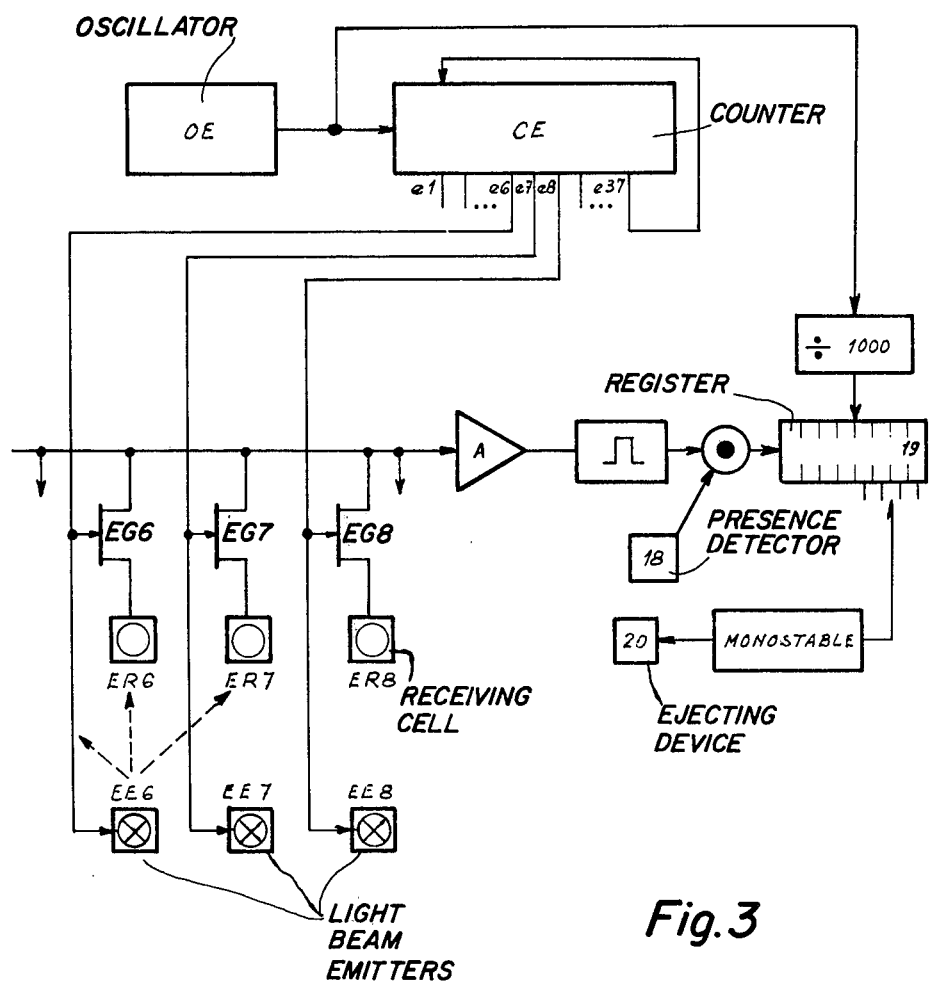
FIG. 3 is a partial schematic diagram of the electronic circuit for the apparatus of FIG. 1 suitable for detecting chipping.

An exemplary suitable electronic circuit is illustrated in FIG. 3. A counter CE, with a base of 37 counts the pulses of a one-megahertz oscillator OE. Each output e1 to e36 energizes the corresponding emitter EE1 to EE36 and simultaneously enables the corresponding gate EG1 to EG36 to read the corresponding receiving cell ER1 to ER36. Output e37 again trips the scanning cycle. The non-detection of a light pulse by a cell generates a signal which, after amplification and shaping, is used, immediately upon validation by the presence detector 18, to actuate through a follow-up register 19, a conventional ejecting device 20 at the apparatus exit.

The entire examination process is carried out in a few milliseconds, so that the longitudinal displacement of the glassware axis XX with respect to the vertical axis of the device remains practically negligible, even in the case of travel speeds in excess of 2,000 glassware items per minute.

The performance figures in this field are limited merely by the response-time delay of the emitters and receivers. For this reason it is preferable to choose emitters and receivers which operate in the infrared spectral region and which are known for their low delay.

In addition, this method of interrogating the cells makes it possible to achieve a very high signal-to-noise ratio.

In light of the fact that the lip of the rim which forms the drinking edge has a surface which is toroidal and not flat, it can be readily appreciated that it is also possible, with suitable disposition of the emitters with respect to the cells, to receive the chip deflected signal on the receiving cell of each radial examining plane which lies closest to the emitter, e.g., cell ER19 for emitter EE1. Such an arrangement is advantageous in the case of certain shapes of rims or defects. It is particularly advantageous for the detection of chips which affect the outer edge of the rim top.

3. Detection of Horizontal Glazes

Figure 11:
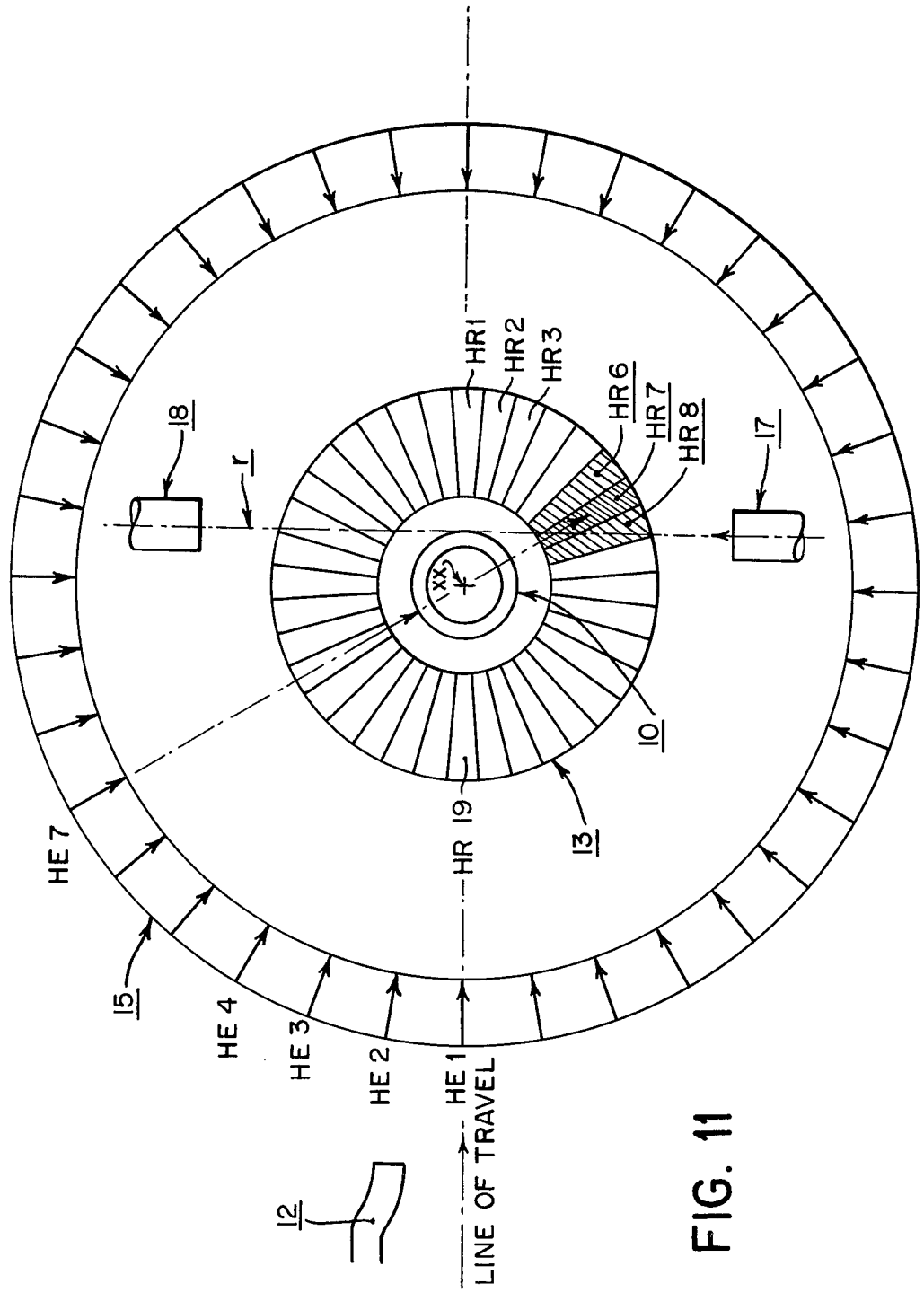
FIG. 11 is a schematic view of the apparatus, in a version which is adapted to detect horizontal glazes, along a plane parallel to the conveyor belt.

In this illustrative embodiment, the receiving cells number 36 and the emitters number 108. As shown in FIG. 11, the 36 receiving cells HR are arranged in a ring about the vertical axis of the glaze detector in the same fashion as the receiving cells ER of the chip detector and, for convenience, the receiving cells will be designated HR1 to HR36.

The 108 emitters are arranged in three concentric circles of 36 emitters as suggested by FIG. 1. These emitters are grouped together to form 36 units HE of three emitters each which are energized in turn during the course of a complete examination cycle. Each of the three emitters of a unit is located in a different one of the three concentric circles and the three emitters are all in the same arc of the circle.

The plan-view drawing of FIG. 11 is therefore identical to FIG. 2 with the EE emitter and the ER cell references replaced by their HE and HR homologs.

The examining process is similar, but the optical arrangement is the reverse of that previously described. During the energization of one three-emitter unit located in a given radial plane, a secondary cycle is carried out during which the 36 cells HR1 to HR36, except for the one or more interdicted cells situated opposite the emitting unit, are successively interrogated.

Thus when, the three emitters of series HE7 are energized, the choice of the interdicted cell or cells can alternatively comprise: (a) cell HR7, or (b) cells HR6, HR7, HR8, or (c) cells HR5, HR6, HR7, HR8, HR9. Those cells are rendered inactive to avoid unwanted reflections from the very surface of the drinking edge or rim and to detect only those reflections which come from the more or less tilted portions that are always found in the so-called "horizontal" glazes.

Figure 4:
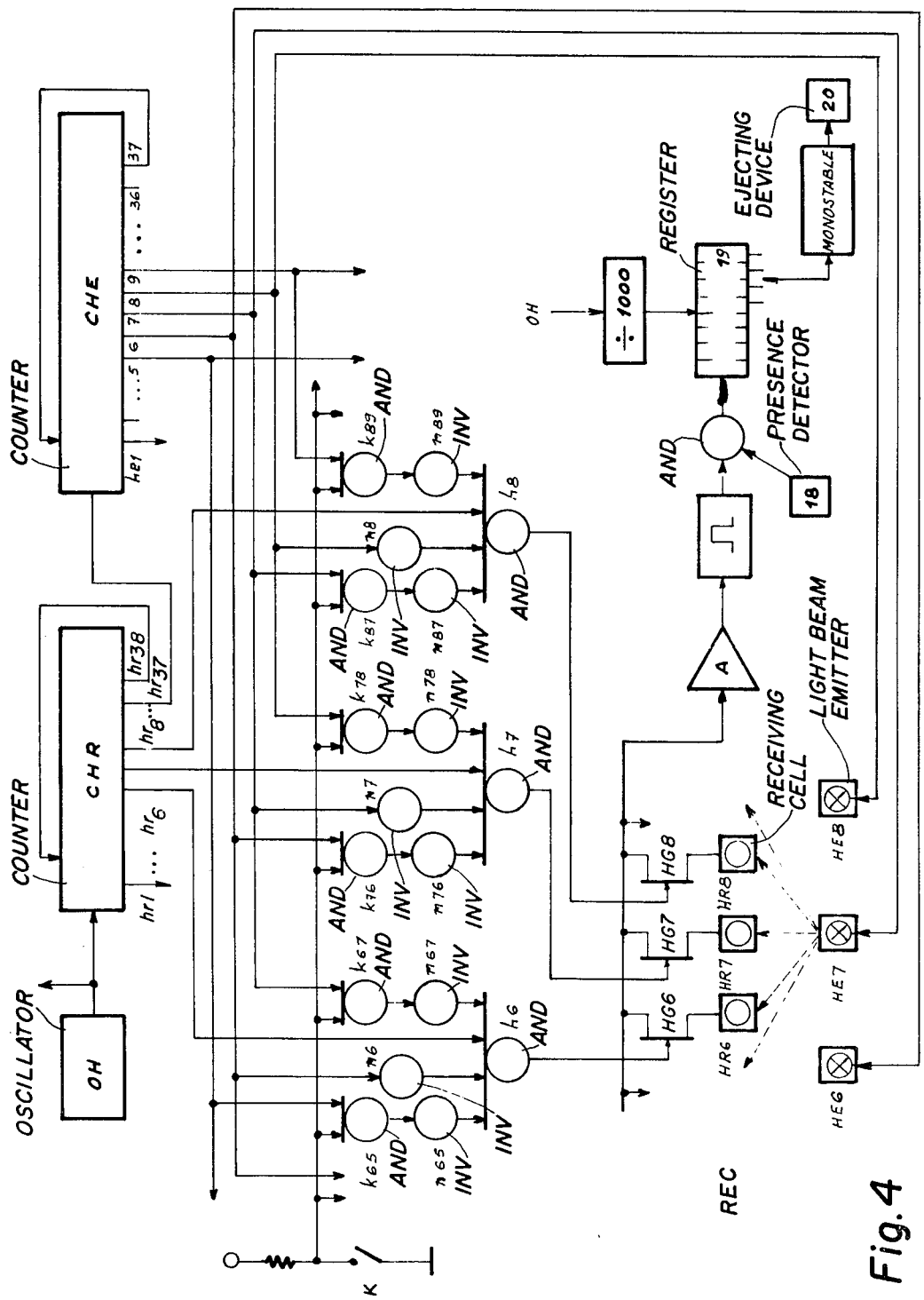
FIG. 4 is a similar electronic schematic diagram suitable for detecting horizontal glazes.

This optical process is carried out by the electronic circuit depicted in FIG. 4.

One counter CHR, with a base of 38, counts the pulses of a three-MHz oscillator OH. Each one of outputs hr1 to hr36 of counter CHR is used to enable, in turn, the reading of the corresponding cells during the course of a secondary cycle. Output hr37 drives a second counter CHE, with a base of 37, successively tripping the excitation of the emitters through the corresponding outputs he1 to he36, while output hr38 retrips the secondary cell reading cycle. After the whole series of emitters has been energized, output he37 retrips, in its turn, the zeroing of counter CHE for the purpose of carrying out a new overall cycle.

In the example which is given in FIG. 4, it can be seen that the reading validation of each of the cells can be interdicted by the conditions which prevail at one of AND gates h1 to h36. Thus, after being inverted by gate n7, signal he7 locks gate h7, thereby interdicting the reading of cell HR7 and, as long as switch K is closed, this interdiction is the only one that exists. If, on the other hand, switch K is open to allow signals he6 and he8 to pass through gates k76 and k78, the reading of cell HR7 is still interdicted when emitters HE6 and HE8 are energized. Reciprocally, when switch K is open and emitter HE7 is energized, cells HR6, HR7, and HR8 are interdicted. As a result of the action represented by the successive switchings of counter HE, it can be seen that the interdicted range changes with the excitation of the emitters.

After amplification and shaping, the possible detection signals of each cell are used in the same way as described in connection with FIG. 3. The cycle times are not greater than approximately thirty nanoseconds, which makes it possible to achieve a scanning speed for the beams of light approaching 140,000 revolutions per minute.

Furthermore, by using a substantial number of detecting areas, through the use of a double detection cycle and also by the creation of at least one dead area opposite each emitter, the cell interrogation method makes it possible to achieve a very favorable signal-to-noise ratio, so that the advantages and the performance figures for this apparatus are nearly comparable to those of the preceding one.

4. Detection of Vertical Glazes

Figure 5:
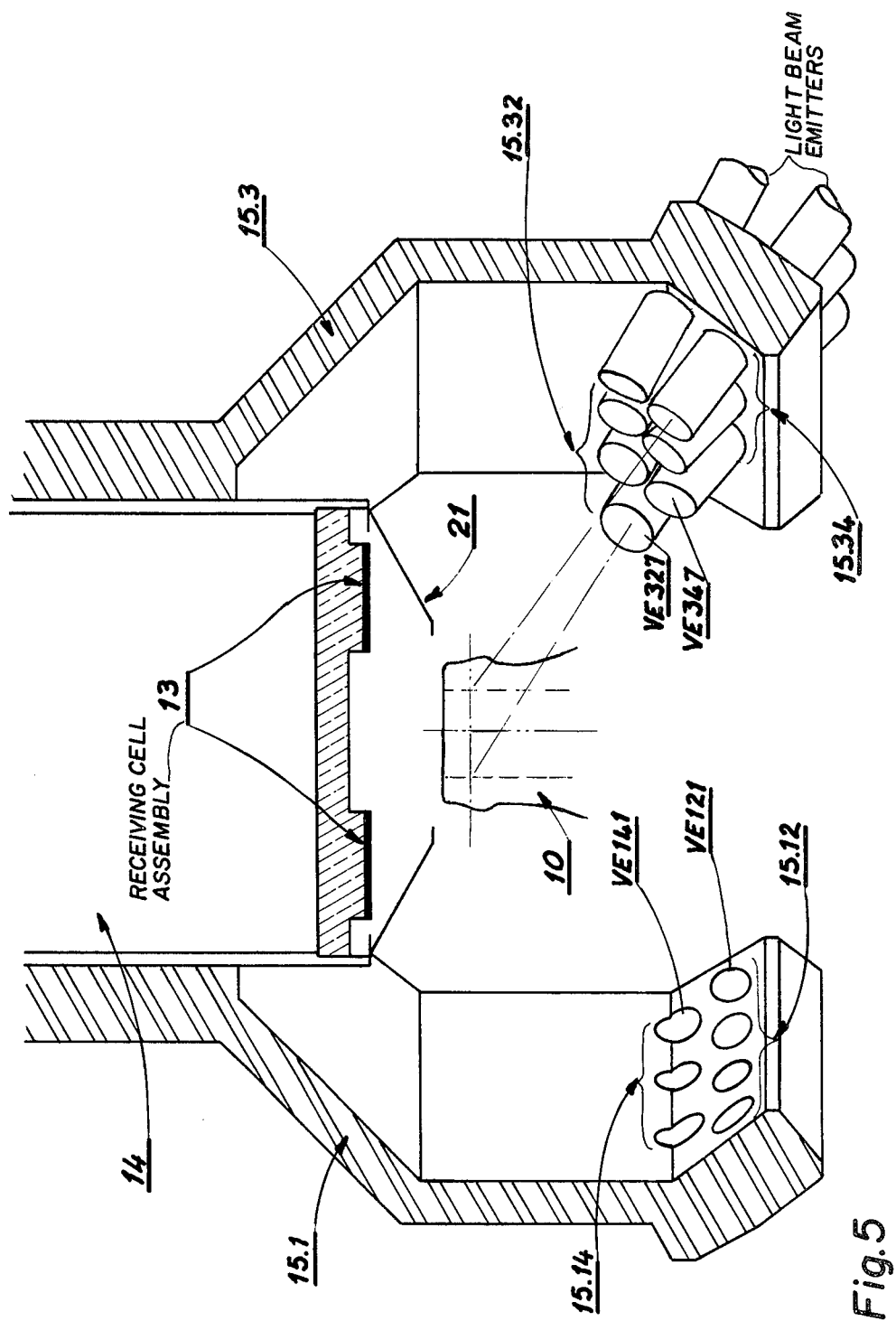
FIG. 5 is a schematic view of the apparatus in a version which is adapted to detect vertical glazes along a transverse plane.
Figure 6:
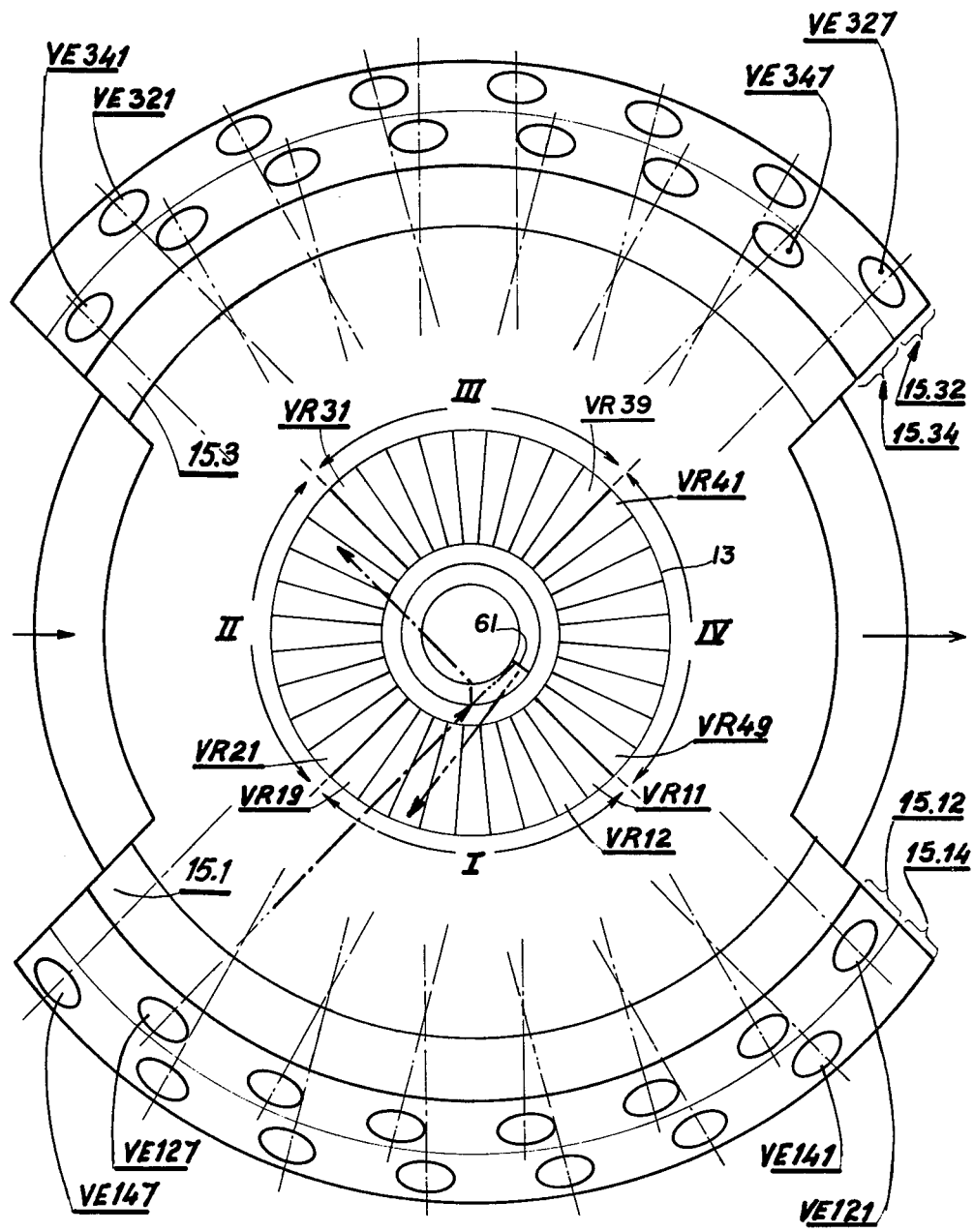
FIG. 6 is a plan view of the apparatus of FIG. 5 from below along a plane parallel to the conveyor belt and passing through the rim of the bottle.

FIGS. 5 and 6 show the optical portion of a device for detecting vertical glazes. The mounting of receiver 13 remains unchanged.

FIG. 5, which is an elevation view projecting along a plane passing through the vertical axis of the device and perpendicular to the line of glassware travel, illustrates the arrangement of the emitters. Illustratively, 28 emitters VE121-127, VE141-147, VE321-327, VE341-347 are arranged in two rows which are slightly displaced with respect to one another. The emitters illuminate in an upward direction the top of the rim of bottle 10, with a tilt from the horizontal that ranges from 30 to 40 degrees. Receiver carrying tube 14 can advantageously be equipped with a mask 21, in the shape of a truncated cone, for reducing the stray illumination.

In order to allow the necks of the bottles to pass through, emitters VE are not arranged in the shape of an enclosed ring but rather, are mounted on two quarter-circle supports 15.1 and 15.3, which are symmetrical with respect to the travel path of bottle 10.

FIG. 6 shows, by projection along a plane which is parallel to the conveyor belt and passes through the rim of the bottle, the arcuate arrangement of the emitters and their orientation with respect to the bottles and to an assembly 13 of 36 receiving cells VR. The 36 receiving cells are split up into four segments I to IV, numbered VR11-19, VR21-29, VR31-39, and VR41-49, respectively. It can be seen that the emitters and receiving cells are not aligned along radial planes. Rather the emitters are aimed so that their beams are substantially tangential to the rim of the bottle at the focusing point. It can also be seen that each emitter array support arm 15.1, 15.3 is made up of two superimposed emitter series 15.12, 15.14 and 15.34, 15.32, which define on the glassware object four illumination regions that are practically symmetrical and, together, cover 360 degrees.

The rationale for choice of the receiving area is set forth in FIG. 6 by the schematic routing of the rays which emanate from one of the emitters and reflect from vertical glaze 61.

Each glaze, depending on its position and its obliquity, may be struck by varying number of emitters. There is an area of stray light around the radial plane of each glaze, and the useful reception area covers an area amounting to approximately one-third of the circle, which, with respect to the glaze, lies behind and to the side.

In operation, the emitters of a given series are energized in turn, and at the time of each energization, only half the cells are interrogated successively, with the other half being interdicted. However, the interdictions do not directly follow the scanning and are carried out by segments. The interdicted-cell area is common to the 7 emitters of a given series. Thus, emitters VE121 to VE127 of series 15.12 are matched by sensitive segments I and II, and hence interdicted cells VR31 to 39 and 41 to 49. Interdicted cells VR21 to 29 and 31 to 39 symmetrically correspond to emitters VE141 to VE147.

The scheme is identical for the second circle arc. Interdicted cells VR11 to 19 and 41 to 49 correspond to emitters VE321 to 327, and interdicted cells VR11 to 19 and 21 to 29 correspond to emitters VE341 to 347, the order of scanning of the four subsequent emitter segments being, of course, immaterial.

Figure 7:
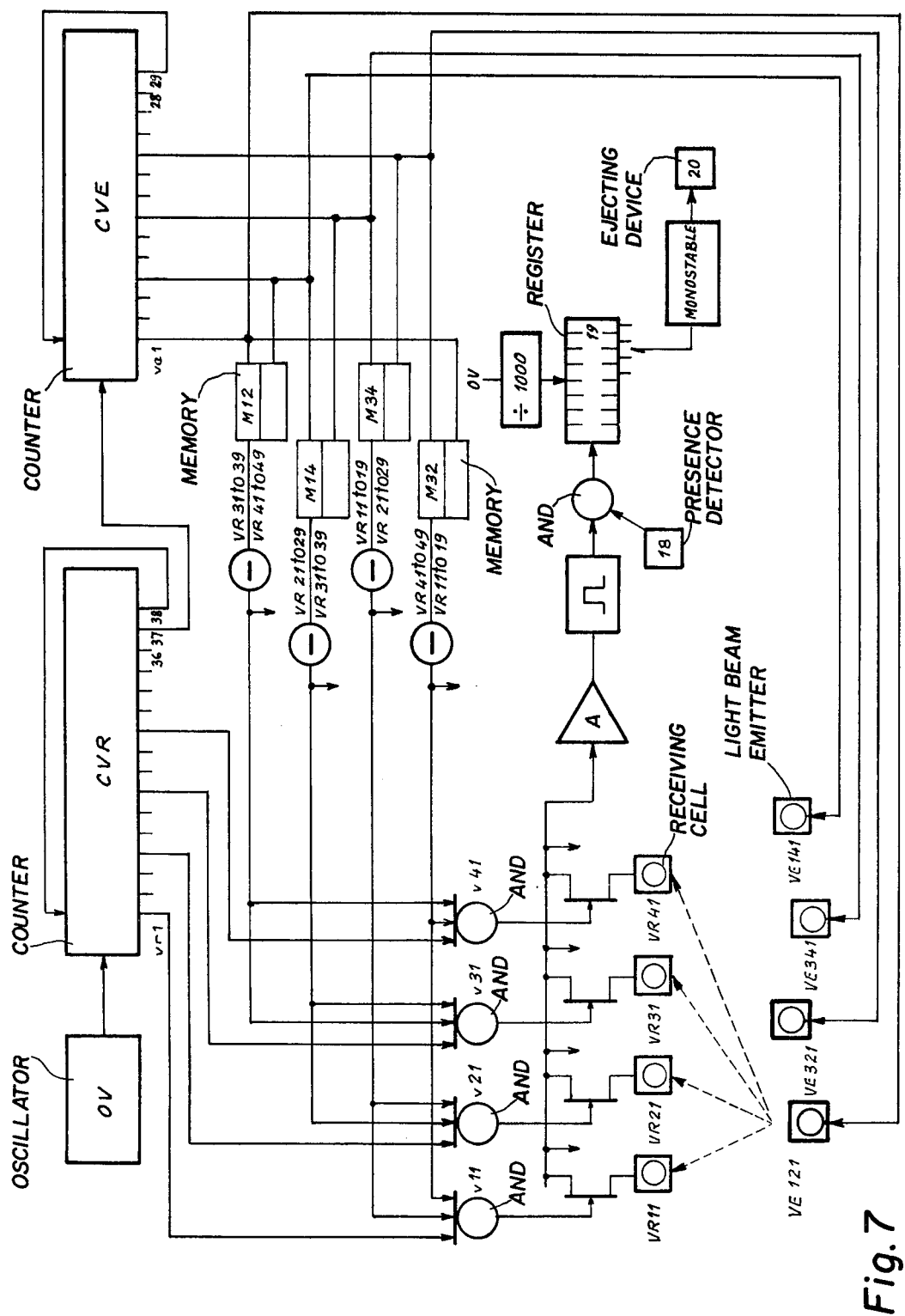
FIG. 7 is a partial schematic diagram of an electronic circuit useful in the apparatus of FIGS. 5 and 6.

This optical process is carried out by an electronic circuit a simplified schematic diagram of which is depicted in FIG. 7.

A 38 base counter CVR counts the pulses of a three-megahertz oscillator OV. Each output vr1 to vr36 of counter CVR validates, in turn, the reading of the 36 cells. Output vr37 drives a second counter, CVE, with a base of 29, subsequently triggering the excitation of the emitters by the corresponding outputs ve1 to ve28. Outputs vr38 and ve29 retrigger the cell-reading cycle and the emitter-energizing cycle, respectively.

According to FIG. 7, it can be seen that each cell's reading validation can be interdicted by the conditions of one of AND gates v11 to 19, 21 to 29, 31 to 39, and 41 to 49, controlled by a set of two memories. For convenience, for each unit of nine receiving cells, FIG. 7 depicts only the first of the gates v11, v21, v31 and v41 and their corresponding control gates VG11, VG21, VG31, VG41 and receiving cells VR11, VR21, VR31, VR41. The function of the other gates and receiving cells in a unit will be apparent. As shown in FIG. 7, gates v11, v21, v31 and v41 are controlled by signals from the pairs of memories M32, M34; M34, M14; M14, M12; M12, M32, respectively. We find, for example, that memory M12 interdicts the reading validation of the cells in segments III and IV, i.e.: VR31 to 49, during the excitation of emitters VE121 to 127, inclusive, in light of the fact that the excitation of emitter VE141 actuates memory M14, which interdicts the reading of cells VR21 to 39, and so on, due to memory M34 and then memory M32.

The signal perceived by each cell is used as described above, and the advantages and performance values of the apparatus are similar.

FIGS. 8 and 9 show a version of the apparatus in which the scanning operation is performed mechanically, by rotating the glassware item beneath a fixed control head. The mechanical driving members are of a conventional type. Accordingly, they are depicted in diagram form by way of a plate 21, associated with a driving roller 22. These members are capable not only of rotating flask 10 but also of causing it to remain beneath the control head during its rotation in order to bring its axis in coincidence with that of the control head. At the rate of travel adopted, it is not possible to utilize continuous movement or travel, since the detection-operation speed would not be sufficient to render negligible the displacements in position between the beginning and the end of the operation. It is therefore essential to immobilize the glassware item for a brief instant, and the detection operation is actuated by a contact when the flask arrives at the proper position beneath the control head.

In the example shown, the different flask-rim controls have been combined in one and the same inspection station.

Receiving surface 23 is made up of a mosaic of cells arranged in the form of a concave cap or dome which partly surrounds the neck of the glassware item in the area to be examined, covering approximately one-third of a turn, and mounted laterally with respect to the path of bottle 10 so as to allow the latter to move through. In the illustrative example of FIGS. 8 and 9, 36 elongated cells DR1 to DR36 are arranged in the form of three superimposed rows: one vertical, one oblique and one horizontal. As shown in FIG. 9, the direction of travel of flask 10 is represented by the dot-dash line and receiving surface 23 is positioned so that it is intersected by the plane transverse to said direction of travel.

The receiving cells are associated with 9 emitters DE1 to DE9, arranged in three columns of three emitters each, which more particularly carry out the detection of horizontal glazes, and with 2 emitters DE10 and DE11, which are more especially intended to detect vertical glazes. The first-mentioned emitters are mounted above the bottle rim, the inside of which they illuminate on either side of the transverse plane of symmetry, and they energize more especially, in the presence of a defect, the cells of the two lower rows of receiving surface 23. The second series of emitters are placed behind the receiving surface 23, at its bottom end and symmetrically with respect to that same plane of symmetry. They energize, more particularly, the cells in the two upper rows of receiving surface 23.

There may, of course, be other emitters, capable of being used or not used depending on the type of glassware items to be checked.

During the course of this control operation the eleven emitters are energized in turn, and during the operation of each of them, all the cells are analyzed in turn.

As in the preceding examples, the light signals are thus linked together in time and not separated in space or through the medium of electronic modulation. This double detecting cycle, of extremely short duration, no longer affects a single type of control along a peripheral area, but rather all of the controls to be carried out along a generatrix. When the examination is completed, the glassware item has undergone a slight rotation whose angle corresponds to the width of the neck perimeter section illuminated by the light beams. A new detecting cycle can be carried out on a slightly displaced segment. It is thus possible to perform a complete scanning operation, in the form of succeeding segments which mutually overlap, so as to lead to an overall examining cycle.

As has already been pointed out, during the excitation of each emitter, such as, for example, emitter DE4, the condition of all of the cells DR1 to DR36 is, as a general rule, fully and completely analyzed, without any of them being assigned to the detection of a specific defect, i.e., without considering the fact that certain cells or even certain rows of cells may never be illuminated by this or that emitter in the presence of a given type of defect.

On the other hand, different cells, may be systematically illuminated by a given emitter, either directly or in the presence of a flawless glassware item. That is why, in accordance with the invention, those cells are interdicted so as to prevent the detection of signals which do not indicate flaws.

Figure 10:
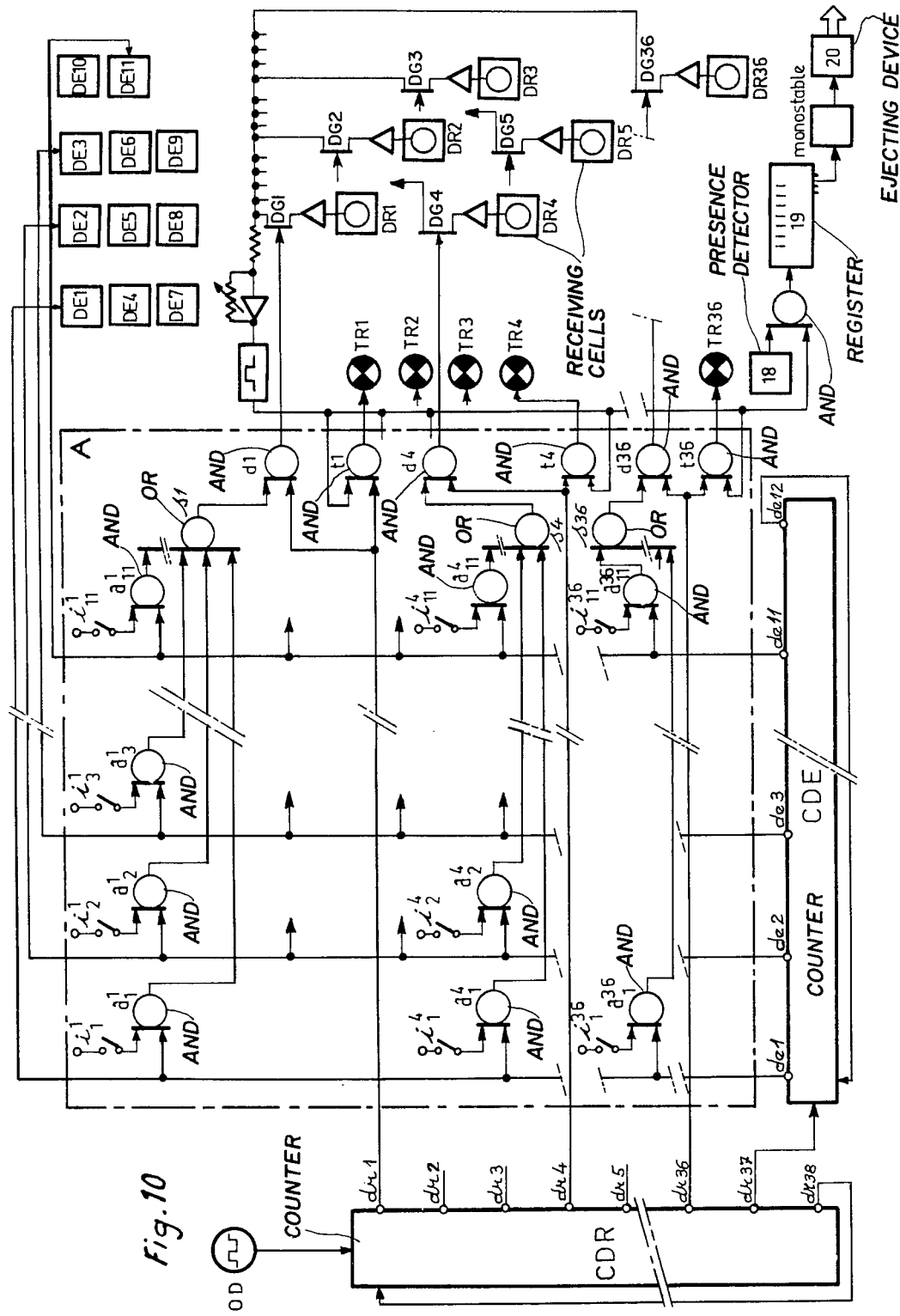
FIG. 10 is a schematic diagram of an electronic circuit useful in the embodiment of FIGS. 8 and 9.

The electronic drive circuit is shown in FIG. 10. In this case, it comprises an 0.5 MHz oscillator OD, which is used as a time base; a 38 position counter CDR, whose purpose is to analyze the 36 cells during the course of each secondary cycle; a second counter CDE, with 12 positions, which triggers the excitation of the 11 emitters in succession; and an operating circuit which is identical to those previously described. Finally, there is an electronic memory circuit which in this case comprises an authorization and interdiction matrix A.

Oscillator OD drives counter CDR, whose outputs dr1 to dr36 produce an analysis of the 36 cells, DR1 to DR36, in succession through AND gates d1 to d36 and control gates DG1 to DG36. Output dr37 drives counter CDE for the purpose of triggering the excitation of the following emitter, and output dr38 returns counter CDR to zero. After the entire series of emitters has been energized, output de12, in its turn, returns counter CDE to zero so that a new detecting cycle can be carried out when the jar or bottle has performed the corresponding rotation.

It can be appreciated from the figure that the reading of the signal emitted by any one of the cells, such as DR4, at the time it is excited by a given emitter, such as DE1, is controlled by an enabling signal sent out to gate d4 by OR gate s4, which is itself fed by AND gates $a_1^4$ to $a_{11}^4$. In turn, each of the 396 AND gates a is enabled by a switch i. Thus, if the switch $i_1^4$ is closed, the output from AND gate $a_1^4$ will enable gate d4 during the time the emitter DE1 is triggered by signal de1 from counter CDE. There is thus established, as was previously the case, a double detecting cycle within which the successive readings of cells DR1 to DR36 are subjected, at the time of the excitation of each emitter DE1 to DE11, to a series of authorizations which are predetermined by the positions assigned to 396 switches $i_1^1$ to $i_{11}^{36}$ on the inside of matrix A.

The signals that are read when control gates DG1 to DG36 are enabled are then amplified, shaped, and validated as in the case of the circuits of FIGS. 3 and 7. The signal is then applied to a register 19 which controls the operations of an ejection device 20.

It will also be noted that each signal that is read when control gates DG1 and DG36 are enabled also enables AND gates t1 to t36. As a result, the signal dr1 to dr36 which enables the detecting cell to be read also causes one of indicating lamps TR1 to TR36 to be lit, signaling which of cells DR1 to DR36 is being read.

The indicating lamps are primarily used for the purpose of quickly identifying those cells which are likely to constitute a source of possible parasitic signals opposite a given emitter in the presence of a flawless glassware item, or even in the absence of any glassware item to be analyzed, in order to interdict, without trial and error, the reading of those cells. The operator is thus in a position to change the interdiction system depending on the nature of the glassware item to be checked.

According to the example under consideration, there is a single row of TR lamps. A gradual survey is therefore conducted, on an emitter-by-emitter basis. Toward that end, all the switches, such as $i_1^1$ to $i_1^{36}$, are, first closed, thereby enabling the reading of all the cells opposite the single emitter DE1. Thereupon, a certain number of flawless glassware items are examined. Any signal which is emitted by cell DR4, for example, causes the corresponding lamp TR4 to light up and indicates that it is necessary to interdict the reading of that cell by opening switch $i_1^4$.

The series of switches $i_2^1$ to $i_2^{36}$ is then set up opposite emitter DE2, and so on until there is a full and complete determination of matrix A.

It is clear that provision could alternatively be made for an indicating matrix complete with TR lamps, and the signals which operate those lamps could be used also to produce the direct opening of the corresponding switches i of matrix A. This also makes it possible to appreciate the great fidelity and the high degree of flexibility of the device.

While the invention has been described in connection with a small number of specific embodiments, it is to be understood that these are merely illustrative of the many other specific embodiments which can also utilize the principles of the invention.

It is possible, without departing from the invention, to build other embodiments which are more particularly adapted to various special cases. For example, an optical device similar to the one described in FIGS. 5 and 6 for detecting vertical glazes, can also be used to detect gaps on the outer surface of the drinking edge or rim, provided detection is authorized only in a narrow set of cells which are mounted to receive direct reflection on a fault-free rim.

It can readily be appreciated that other modifications of the device described herein will make it possible to carry out inspection and control of the shoulders of a jar or flask or the bottom of a bottle.

It should also be understood that it is possible to combine the optical members in a different fashion, as by juxtaposing several types of controls in one inspection station, thereby combining radial and peripheral scanning. Because of the interlacing of the signals, there is no risk of reciprocal parasitic oscillations, and the only problem consists in placing the necessary number of emitters in the desired positions, within the limits permitted by the glassware travel speed.

Conversely, if a mechanical scanning operation is carried out by rotating the glassware item to be examined beneath the control head, the number of emitters can be reduced to a point where only one simple or complex light beam is used for the purpose of detecting rim breaks or gaps, or three beams scanning the entire neck from different angles are used for detecting horizontal glazes or, finally, two symmetrical light beams are used for detecting vertical glazes. The superimposing of different controls at one and the same control station then becomes much easier, since there is more flexibility in setting up the emitters and receivers. This makes it possible to direct them at more favorable angles in the case of certain difficult control operations. Although there continue to be, as has just been pointed out, certain lighting angles which are more favorable than others for examining such a defect, emitters and receivers may thus lose a portion of their specific nature, and the entire cell-mosaic surface can be analyzed during the course of each emitting phase. In such arrangements, the emitter-excitation cycle is no longer used to create a peripheral scanning, but rather to bring together the different controls onto a revolution fraction.

The mechanical scanning embodiment also offers the advantage of simplifying the electronic circuit, and, although it does not lend itself to control operations performed at speeds of travel which are as high as those encountered in bottling plants, it does operate at a speed which is sufficient for working conveniently at production-line outlets.

Thus, numerous and varied devices can be made by those skilled in the art without departing from the spirit and scope of the present invention.

I claim:

1. Apparatus for continuously inspecting transparent objects having at least a localized region with symmetry of revolution about an axis comprising:
    a plurality of fixed light beam emitters for directing light beams at the position where a transparent object is located for inspection;
    a plurality of light-detecting means generally oriented with respect to said light beam emitters so that at least some light-detecting means receive light from said light beam emitters when a transparent object is located at said inspection position;

electronic means for sequentially activating said light beam emitters and for interrogating said light-detecting means in a circular scanning examination cycle, said electronic means further comprising first and second looped counters, said first counter transmitting cycles of excitation orders to said light beam emitters and said second counter transmitting cycles of interrogation orders to said light-detecting means, said counters being interconnected so that one of said counters transmits incrementing instructions to the other of said counters after transmitting a cycle of orders.

2. Apparatus according to claim 1 further characterized by the presence of gate means between said second counter and said light-detecting means for permitting selection of those detecting means to be read.

3. Apparatus according to claim 2 further comprising memory means for controlling said gate means and matrix means, including memory means, for combining light beam emitter excitation signals and light-detector output signals by means of the memory-controlled gate means.

4. Apparatus according to claim 2 further comprising a plurality of indicating means for indicating those light detecting means which produce a rejection signal wherein said gate means and said indicating means are controlled by the same signal.

5. Apparatus according to claim 2 further comprising a plurality of indicating means for indicating those light-detecting means which produce a rejection signal.

6. Apparatus according to claim 1 wherein said electronic means comprises memory means for authorizing detection during each illumination step by selected ones of said plurality of light-detection means.

7. Apparatus according to claim 6 further comprising an auxiliary interdiction means for permitting selection of the light-detecting means to be interdicted.

8. Apparatus according to claim 1 wherein said electronic means further comprises means for inhibiting the interrogation of individual light-detecting means.

9. Apparatus according to claim 8 further comprises memory means which may be selectively programmed so as to inhibit selected light-detecting means when particular light beam emitters are activated.

10. Apparatus according to claim 1 wherein said electronic means further comprises:
gate means between said second counter and said light-detecting means for permitting selection of those light-detecting means to be interrogated; and
matrix means, including memory means for controlling said gate means, whereby selected gates are inhibited when individual light beam emitters are activated.

11. Apparatus according to claim 1 further comprising means for indicating which light detecting means produces an output signal when a light beam emitter is energized.

12. Apparatus for continuously inspecting transparent objects having at least a localized region with symmetry of revolution about an axis comprising:
a plurality of fixed light beam emitters for directing light beams at the position where a transparent object is located for inspection;
a plurality of light-detecting means generally oriented with respect to said light beam emitters so that at least some light-detecting means receive light from said light beam emitters when a transparent object is located at said inspection position;
first electronic means for successively activating said light beam emitters one at a time and for interrogating said light-detecting means in a scanning examination cycle; and
second electronic means including a programmable memory means for inhibiting the interrogation of different selected light-detecting means when different light beam emitters are activated.

13. Apparatus for continuously inspecting bottles for chipped rims, said apparatus comprising:
a plurality of fixed light beam emitters for directing light beams at the position where the bottle is located for inspection, said light beam emitters being located above the bottle when it is in said inspection position, said light beam emitters being aimed at different portions of the rim of the bottle when it is located in said inspection position and the totality of said light beam emitters illuminating the entire rim of said bottle;
a plurality of fixed light-detecting means arranged in a ring and paired with said light beam emitters, each one of said light-detecting means being oriented so that it receives light from a different one of said light beam emitters when a bottle without a chipped rim is located at said inspection position, said light-detecting means being located above the bottle when it is in said inspection position;
first electronic means for successively activating said light beam emitters one at a time and for simultaneously interrogating said paired light-detecting means in an examination cycle; and
second electronic means for generating a reject signal if light is not sensed by a light-detecting means when its paired light beam emitter is activated.

14. Apparatus for continuously inspecting the rim of bottles for horizontal glazes, said apparatus comprising
a plurality of fixed light beam emitters for directing light beams at the position where the bottle is located for inspection, said light beam emitters being located above the bottle when it is in said inspection position, said light beam emitters being aimed at different portions of the rim of the bottle when it is located in said inspection position and the totality of said light beam emitters illuminating the entire rim of said bottle;
a plurality of fixed light-detecting means arranged in a ring and paired with said light beam emitters, each one of said light-detecting means being oriented so that it receives light from a different one of said light beam emitters when a bottle without a horizontal glaze is located at said inspection position, said light-detecting means being located above the bottle when it is in said inspection position;
first electronic means for successively activating said light beam emitters one at a time and for interrogating some, but not all, of said light-detecting means while each light beam emitter is activated, said means not interrogating the light-detecting means that is paired with the light beam emitter that is activated; and
second electronic means for generating a reject signal if light is sensed by one of the interrogated light-detecting means.

15. Apparatus for continuously inspecting the rim of bottles for horizontal glazes, said apparatus comprising:
a plurality of fixed light beam emitters for directing light beams at the position where the bottle is located for inspection, said light beam emitters being located above the bottle when it is in said inspection position, said light beam emitters being aimed at different portions of the rim of the bottle when it is located in said inspection position and the totality of said light beam emitters illuminating the entire rim of said bottle;

a plurality of fixed light-detecting means arranged in a ring and generally oriented so that a least some light-detecting means receive light from said light beam emitters when a bottle without a horizontal glaze is located at said inspection position;

first electronic means for successively activating said light beam emitters one at a time and for interrogating a portion of said light-detecting means while each light beam emitter is activated, said portion being that part which would receive no light from the light beam emitter in the case of a bottle which did not contain a horizontal glaze; and second electronic means for generating a reject signal if light is sensed by one of the interrogated light-detecting means.

16. Apparatus for continuously inspecting the rim of bottles for vertical glazes, said apparatus comprising:

a plurality of fixed light beam emitters for directing light beams at the position where the bottle is located for inspection, said light beam emitters being located below the rim of the bottle when it is in said inspection position, said light beam emitters being aimed at different portions of the rim of the bottle when it is located in said inspection station and the totality of said light beam emitters illuminating the entire rim of said bottle;

a plurality of fixed light-detecting means arranged in a ring and generally oriented so that a least some light-detecting means receive light from said light beam emitters when a bottle is located at said inspection position, said light detecting means being located above the rim of the bottle when it is in said inspection position;

first electronic means for successively activating said light beam emitters one at a time and for interrogating a portion of said light-detecting means while each light beam emitter is activated, said portion being that part which would receive no light from the light beam emitter in the case of a bottle which did not contain a vertical glaze; and second electronic means for generating a reject signal if light is sensed by one of the interrogated light-detecting means.

17. Apparatus for inspecting a transparent object for chipping or glazes, said apparatus comprising:

a plurality of fixed light beam emitters for directing light beams at the position where the object is located for inspection, a first group of said light beam emitters being located above the object and a second group being located below the upper surface of the object when it is in said inspection position, said light beam emitters in said first group being aimed at different portions on a periphery of the object when it is located in said inspection station and the totality of said first group of light beam emitters illuminating the entire periphery of said object and said light beam emitters in said second group being aimed at different portions on a periphery of the object when it is located in said inspection station and the totality of said second group of light beam emitters illuminating the entire periphery of the object;

a first plurality of light-detecting means arranged opposite said first group of emitters and below the upper surface of the object so that the inspection station is therebetween and generally oriented so that a least some light-detecting means receive light from said light beam emitters when the object is located at said inspection position;

a second plurality of light-detecting means oriented in a substantially horizontal plane, said second light detecting means being located above the upper surface of the object when it is in said inspection position;

first electronic means for successively activating said light beam emitters one at a time and for simultaneously interrogating said light-detecting means in an examination cycle; and second electronic means for producing a reject signal if a light pattern is detected that corresponds to that of a defect in the object.

18. Apparatus according to any one of claims 1, 12, 13, 14 or 15 wherein said fixed light beam emitters are arranged in a first ring about said inspection position and said light-detecting means are arranged in a second ring about said inspection position.

19. Apparatus according to any one of claims 1, 12, 14 or 15 wherein a first group of fixed light beam emitters are aimed at said inspection position at a first angle with respect to the vertical and a second group of said fixed light beam emitters are aimed at said inspection position at a second angle with respect to the vertical.

20. Apparatus according to any one of claims 12, 16 or 17 wherein said first electronic means further comprises first and second looped counters, said first counter transmitting cycles of excitation orders to said light beam emitters and said second counter transmitting cycles of interrogation orders to said light-detecting means, said counters being interconnected so that one of said counters transmits incrementing instructions to the other of said counters after transmitting a cycle of orders.

21. A method for continuously inspecting bottles for chipped rims using an inspection station comprising a plurality of fixed light beam emitters for illuminating a bottle and a plurality of fixed light-sensitive receivers for detecting light from said bottle, said method comprising the steps of:

transporting said bottle to said inspection station;

successively illuminating the rim of said bottle one circumferential portion at a time about said bottle by activating said light beam emitters one at a time;

successively interrogating said light-sensitive receivers one at a time, a different receiver being interrogated for each different circumferential portion that is illuminated; and rejecting said bottle if light is not detected by said receivers.

22. A method of continuously inspecting bottles for horizontal glazes in the vicinity of their rims using an inspection station comprising a plurality of fixed light beam emitters for illuminating a bottle and a plurality of light-sensitive receivers for detecting light from said bottle, said method comprising the steps of:

transporting said bottle to said inspection station;

successively illuminating the rim of said bottle one circumferential portion at a time about said bottle by activating said light beam emitters one at a time;

successively interrogating some, but not all, of said light-sensitive receivers one at a time during the illumination of each respective circumferential portion, the receivers that are not interrogated being those where light from the illuminated circumferential portion would fall if there were no horizontal glaze; and rejecting said bottle if light is detected by the interrogated receivers.

23. The method of claim 22 further characterized in that:

said object is transported continuously through said inspection station without rotation; and said object is illuminated by circularly scanning a series of fixed light beams oriented at substantially the same angle with respect to the axis of symmetry of said object but forming a plurality of different angles with respect to the direction of travel of said object.

24. A method of continuously inspecting bottles for vertical glazes in the vicinity of their rims using an inspection station comprising a plurality of fixed light beam emitters for illuminating a bottle and a plurality of fixed light-sensitive receivers for detecting light from said bottle, said method comprising the steps of:

transporting said bottle to said inspection station;

successively illuminating the rim of said bottle one circumferential portion at a time about said bottle by activating said light beam emitters one at a time;

successively interrogating a portion of said light-sensitive receivers during the illumination of each respective circumferential portion, the receivers that are not interrogated being those where light from the illuminated circumferential portion would fall if there were no vertical glaze; and rejecting said bottle if light is detected by the interrogated receivers.

25. A method of continuously inspecting bottles using an inspection station comprising a plurality of fixed light beam emitters for illuminating a bottle and a plurality of light-sensitive receivers for detecting light from said bottle, said method comprising the steps of:

transporting said bottle to said inspection station;

successively illuminating the rim of said bottle one circumferential portion at a time about said bottle by activating said light beam emitters one at a time;

successively interrogating a portion of said light-sensitive receivers during the illumination of each respective circumferential portion;

controlling said illuminating and interrogating steps by first and second looped counters, said first counter transmitting cycles of excitation orders to said light beam emitters and said second counter transmitting cycles of interrogation orders to said light-detecting means, said counters being interconnected so that one of said counters transmits incrementing instructions to the other after transmitting a cycle of orders; and rejecting said bottle if a light pattern detected by the interrogated receivers is representative of a defect.

26. A method of inspecting transparent objects using an inspection station comprising a plurality of fixed light beam emitters for illuminating the object and a plurality of light-sensitive receivers for detecting light from said object, said method comprising the steps of:

transporting said object to said inspection station;

successively illuminating one circumferential portion of said object at a time by activating said light beam emitters one at a time;

successively interrogating a portion of said light-sensitive receivers during the illumination of each respective circumferential portion;

controlling said illuminating and interrogating steps by first and second looped counters, said first counter transmitting cycles of excitation orders to said light beam emitters and said second counter transmitting cycles of interrogation orders to said light-detecting means, said counters being interconnected so that said second counter transmits incrementing instructions to said first counter after transmitting a cycle of orders; and rejecting said object if a light pattern detected by the interrogated receivers is representative of a defect.

27. The method of claim 26 further comprising the step of rotating the object after the first counter transmits a cycle of orders and repeating the steps of successively illuminating one circumferential portion of the object at a time and successively interrogating a portion of said light-sensitive receivers, whereby a different part of the object is inspected.

28. Apparatus for continuously inspecting the rim of bottles for horizontal glazes, said apparatus comprising:

a plurality of fixed light beam emitters for directing light beams at the position where the bottle is located for inspection, said light beam emitters being located above the bottle when it is in said inspection position;

a plurality of light-detecting means arranged in a ring and paired with said light beam emitters, each one of said light-detecting means being oriented so that it receives light from a different one of said light beam emitters when a bottle without a horizontal glaze is located at said inspection position, said light-detecting means being located above the bottle when it is in said inspection position;

first electronic means for successively activating said light beam emitters one at a time and for interrogating some, but not all, of said light-detecting means while each light beam emitter is activated, said means not interrogating the light-detecting means that is paired with the light beam emitter that is activated, said first electronic means further comprising first and second looped counters, said first counter transmitting cycles of excitation orders to said light beam emitters and said second counter transmitting cycles of interrogation orders to said light-detecting means, said counters being interconnected so that one of said counters transmits incrementing instructions to the other of said counters after transmitting a cycle of orders; and second electronic means for generating a reject signal if light is sensed by one of the interrogated light-detecting means.

29. Apparatus for continuously inspecting the rim of bottles for horizontal glazes, said apparatus comprising:

a plurality of fixed light beam emitters for directing light beams at the position where the bottle is located for inspection, said light beam emitters being located above the bottle when it is in said inspection position;

a plurality of light-detecting means arranged in a ring and generally oriented so that at least some light-detecting means receive light from said light beam emitters when a bottle without a horizontal glaze is located at said inspection position;

first electronic means for successively activating said light beam emitters one at a time and for interrogating a portion of said light-detecting means while each light beam emitter is activated, said portion being that part which would receive no light from the light beam emitter in the case of a bottle which did not contain a horizontal glaze, said first electronic means further comprising first and second looped counters, said first counter transmitting cycles of excitation orders to said light beam emitters and said second counter transmitting cycles of interrogation orders to said light-detecting means, said counters being interconnected so that one of said counters transmits incrementing instructions to the other of said counters after transmitting a cycle of orders; and second electronic means for generating a reject signal if light is sensed by one of the interrogated light-detecting means.

30. Apparatus for continuously inspecting the rim of bottles for vertical glazes, said apparatus comprising:

a plurality of fixed light beam emitters for directing light beams at the position where the bottle is located for inspection, said light beam emitters being located below the rim of the bottle when it is in said inspection position;

a plurality of light-detecting means arranged in a ring and generally oriented so that a least some light-detecting means receive light from said light beam emitters when a bottle is located at said inspection position, said light detecting means being located above the rim of the bottle when it is in said inspection position;

first electronic means for successively activating said light beam emitters one at a time and for interrogating a portion of said light-detecting means while each light beam emitter is activated, said portion being that part which would receive no light from the light beam emitter in the case of a bottle which did not contain a vertical glaze, said first electronic means further comprising first and second looped counters, said first counter transmitting cycles of excitation orders to said light beam emitters and said second counter transmitting cycles of interrogation orders to said light-detecting means, said counters being interconnected so that one of said counters transmits incrementing instructions to the other of said counters after transmitting a cycle of orders; and second electronic means for generating a reject signal if light is sensed by one of the interrogated light-detecting means.

31. Apparatus for inspecting a transparent object for chipping or glazes, said apparatus comprising:

a plurality of fixed light beam emitters for directing light beams at the position where the object is located for inspection, a first group of said light beam emitters being located above the object and a second group being located below the upper surface of the object when it is in said inspection position;

a first plurality of light-detecting means arranged opposite said first group of emitters so that the inspection station is therebetween and generally oriented so that a least some light-detecting means receive light from said light beam emitters when the object is located at said inspection position;

a second plurality of light-detecting means oriented in a substantially horizontal plane, said second light detecting means being located above the upper surface of the object when it is in said inspection position;

first electronic means for successively activating said light beam emitters one at a time and for simultaneously interrogating said light-detecting means in an examination cycle, said first electronic means further comprising first and second looped counters, said first counter transmitting cycles of excitation orders to said light beam emitters and said second counter transmitting cycles of interrogation orders to said light-detecting means, said counters being interconnected so that one of said counters transmits incrementing instructions to the other of said counters after transmitting a cycle of orders;

second electronic means for producing a reject signal if a light pattern is detected that corresponds to that of a defect in the object.

32. The apparatus of claim 31 further comprising means for rotating the object when it is in the inspection position.

33. Apparatus for continuously inspecting transparent objects comprising:

a plurality of fixed light beam emitters for directing light beams at the position where a transparent object is located for inspection;

a plurality of light-detecting means generally oriented with respect to said light beam emitters so that at least some light-detecting means receive light from said light beam emitters when a transparent object is located at said inspection position;

first electronic means for successively activating said light beam emitters one at a time and for interrogating said light-detecting means in a scanning examination cycle; and second electronic means including a programmable memory means for inhibiting the interrogation of different selected light-detecting means when different light beam emitters are activated.

* * * * *

UNITED STATES PATENT AND TRADEMARK OFFICE
CERTIFICATE OF CORRECTION

PATENT NO. : 4,293,219
DATED : October 6, 1981
INVENTOR(S) : Marcel Ducloux

It is certified that error appears in the above—identified patent and that said Letters Patent is hereby corrected as shown below:

Column 14, lines 62-3, "of light-sensitive" should read
-- of fixed light-sensitive --

Signed and Sealed this

Second Day of February 1982

[SEAL]

Attest:

Attesting Officer

GERALD J. MOSSINGHOFF
Commissioner of Patents and Trademarks